US010186760B2

(12) United States Patent
Heppell

(10) Patent No.: US 10,186,760 B2
(45) Date of Patent: Jan. 22, 2019

(54) ANTENNA DESIGNS FOR COMMUNICATION BETWEEN A WIRELESSLY POWERED IMPLANT TO AN EXTERNAL DEVICE OUTSIDE THE BODY

(71) Applicant: Thoratec Corporation, Pleasanton, CA (US)

(72) Inventor: Kevin Gerald Heppell, Oakland, CA (US)

(73) Assignee: TC1 LLC, St. Paul, MN (US)

( * ) Notice: Subject to any disclaimer, the term of this patent is extended or adjusted under 35 U.S.C. 154(b) by 481 days.

(21) Appl. No.: 14/861,977

(22) Filed: Sep. 22, 2015

(65) Prior Publication Data

US 2016/0087331 A1    Mar. 24, 2016

Related U.S. Application Data

(60) Provisional application No. 62/053,663, filed on Sep. 22, 2014.

(51) Int. Cl.
  *H01Q 1/27*    (2006.01)
  *H01Q 1/24*    (2006.01)
  (Continued)

(52) U.S. Cl.
  CPC ......... *H01Q 1/273* (2013.01); *A61N 1/37229* (2013.01); *H01Q 1/2225* (2013.01);
  (Continued)

(58) Field of Classification Search
  CPC ...... H01Q 1/273; H01Q 9/0407; H01Q 9/065; A61N 1/37229; A61N 1/3752–1/3758; A61N 1/3968
  See application file for complete search history.

(56) References Cited

U.S. PATENT DOCUMENTS

| 4,041,955 A | 8/1977 | Kelly et al. |
| 4,352,960 A | 10/1982 | Dormer et al. |

(Continued)

FOREIGN PATENT DOCUMENTS

| DE | 202012000166 U1 | 6/2013 |
| DE | 102012201073 A1 | 7/2013 |

(Continued)

OTHER PUBLICATIONS

Development and Implementation of RFID Technology, Ed. Cristina Turcu, Feb. 2009, pp. 28-30, 93-97.

(Continued)

*Primary Examiner* — Jessica Han
*Assistant Examiner* — Amal Patel
(74) *Attorney, Agent, or Firm* — Armstrong Teasdale LLP

(57) ABSTRACT

Methods and apparatus for wireless power transfer and communications are provided. In one embodiment, a wireless power transfer system comprises an external transmit resonator configured to transmit wireless power, an implantable receive resonator configured to receive the transmitted wireless power from the transmit resonator, and communications antenna in the implantable receive resonator configured to send communication information to the transmit resonator. The communications antenna can include a plurality of gaps positioned between adjacent conductive elements, the gaps being configured to prevent or reduce induction of current in the plurality of conductive elements when the antenna is exposed to a magnetic field.

8 Claims, 9 Drawing Sheets

(51) Int. Cl.
*H01Q 1/50* (2006.01)
*H01Q 1/52* (2006.01)
*H02J 5/00* (2016.01)
*H02J 7/02* (2016.01)
*A61N 1/372* (2006.01)
*H04B 5/00* (2006.01)
*H02J 50/40* (2016.01)
*H02J 50/12* (2016.01)
*H01Q 1/22* (2006.01)
*H01Q 1/36* (2006.01)

(52) U.S. Cl.
CPC ................ *H01Q 1/24* (2013.01); *H01Q 1/36* (2013.01); *H01Q 1/50* (2013.01); *H01Q 1/526* (2013.01); *H02J 50/12* (2016.02); *H02J 50/40* (2016.02); *H04B 5/0037* (2013.01)

(56) References Cited

U.S. PATENT DOCUMENTS

| | | |
|---|---|---|
| 4,561,443 A | 12/1985 | Hogrefe et al. |
| 4,561,444 A | 12/1985 | Livingston et al. |
| 4,630,615 A | 12/1986 | Yomtov |
| 4,679,560 A | 7/1987 | Galbraith |
| 4,726,378 A | 2/1988 | Kaplan |
| 4,736,747 A | 4/1988 | Drake |
| 4,924,171 A | 5/1990 | Baba et al. |
| 4,945,305 A | 7/1990 | Blood |
| 5,070,223 A | 12/1991 | Colasante |
| 5,333,095 A | 7/1994 | Stevenson et al. |
| 5,346,458 A | 9/1994 | Affeld |
| 5,350,413 A | 9/1994 | Miller et al. |
| 5,569,156 A | 10/1996 | Mussivand |
| 5,630,836 A | 5/1997 | Prem et al. |
| 5,690,693 A | 11/1997 | Wang et al. |
| 5,702,431 A | 12/1997 | Wang et al. |
| 5,755,748 A | 5/1998 | Borza |
| 5,771,438 A | 6/1998 | Palermo et al. |
| 5,831,248 A | 11/1998 | Hojyo et al. |
| 5,867,361 A | 2/1999 | Wolf et al. |
| 5,948,006 A | 9/1999 | Mann |
| 6,123,726 A | 9/2000 | Mori et al. |
| 6,149,683 A | 11/2000 | Lancisi et al. |
| 6,212,430 B1 | 4/2001 | Kung |
| 6,296,533 B1 | 10/2001 | Grubbs et al. |
| 6,312,338 B1 | 11/2001 | Sato et al. |
| 6,320,354 B1 | 11/2001 | Sengupta et al. |
| 6,324,431 B1 | 11/2001 | Zarinetchi et al. |
| 6,327,504 B1 | 12/2001 | Dolgin et al. |
| 6,389,318 B1 | 5/2002 | Zarinetchi et al. |
| 6,400,991 B1 | 6/2002 | Kung |
| 6,442,434 B1 | 8/2002 | Zarinetchi et al. |
| 6,451,055 B1 | 9/2002 | Weiss |
| 6,458,164 B1 | 10/2002 | Weiss |
| 6,478,820 B1 | 11/2002 | Weiss |
| 6,553,263 B1 | 4/2003 | Meadows et al. |
| 6,579,315 B1 | 6/2003 | Weiss |
| 6,591,139 B2 | 7/2003 | Loftin et al. |
| 6,605,032 B2 | 8/2003 | Benkowski et al. |
| 6,647,298 B2 | 11/2003 | Abrahamson et al. |
| 6,650,213 B1 | 11/2003 | Sakurai et al. |
| 6,723,039 B2 | 4/2004 | French et al. |
| 6,772,011 B2 | 8/2004 | Dolgin |
| 6,801,807 B2 | 10/2004 | Abrahamson |
| 6,810,289 B1 | 10/2004 | Shaquer |
| 6,850,803 B1 | 2/2005 | Jimenez et al. |
| 6,894,456 B2 | 5/2005 | Tsukamoto et al. |
| 6,895,281 B1 | 5/2005 | Amundson et al. |
| 6,949,065 B2 | 9/2005 | Sporer et al. |
| 6,960,968 B2 | 11/2005 | Odenaal et al. |
| 6,967,621 B1 | 11/2005 | Cadotte, Jr. et al. |
| 6,985,773 B2 | 1/2006 | Von Arx et al. |
| 7,015,769 B2 | 3/2006 | Schulman et al. |
| 7,107,103 B2 | 9/2006 | Schulman et al. |
| 7,126,310 B1 | 10/2006 | Barron |
| 7,225,032 B2 | 5/2007 | Schmeling et al. |
| 7,246,040 B2 | 7/2007 | Borg et al. |
| 7,286,880 B2 | 10/2007 | Olson et al. |
| 7,428,438 B2 | 9/2008 | Parramon et al. |
| 7,471,986 B2 | 12/2008 | Hatlestad |
| 7,496,733 B2 | 2/2009 | Altman et al. |
| 7,505,816 B2 | 3/2009 | Schmeling et al. |
| 7,515,012 B2 | 4/2009 | Schulman et al. |
| 7,522,878 B2 | 4/2009 | Baarman |
| 7,532,901 B1 | 5/2009 | Lafranchise et al. |
| 7,565,187 B1 | 7/2009 | Dynok et al. |
| 7,571,007 B2 | 8/2009 | Erickson et al. |
| 7,574,173 B2 | 8/2009 | Terranova et al. |
| 7,587,241 B2 | 9/2009 | Parramon et al. |
| 7,599,743 B2 | 10/2009 | Hassler et al. |
| 7,650,187 B2 | 1/2010 | Gruber et al. |
| 7,650,192 B2 | 1/2010 | Wahlstrand |
| 7,711,433 B2 | 5/2010 | Davis et al. |
| 7,720,546 B2 | 5/2010 | Ginggen et al. |
| 7,741,734 B2 | 6/2010 | Joannopoulos et al. |
| 7,761,164 B2 | 7/2010 | Verhoef et al. |
| 7,774,069 B2 | 8/2010 | Olson et al. |
| 7,782,190 B1 | 8/2010 | Martin et al. |
| 7,805,200 B2 | 9/2010 | Kast et al. |
| 7,812,481 B2 | 10/2010 | Iisaka et al. |
| 7,818,036 B2 | 10/2010 | Lair et al. |
| 7,818,037 B2 | 10/2010 | Lair et al. |
| 7,825,543 B2 | 11/2010 | Karalis et al. |
| 7,830,114 B2 | 11/2010 | Reed |
| 7,865,245 B2 | 1/2011 | Torgerson et al. |
| 7,872,367 B2 | 1/2011 | Recksiek et al. |
| 7,904,170 B2 | 3/2011 | Harding |
| 7,932,696 B2 | 4/2011 | Peterson et al. |
| 7,962,222 B2 | 6/2011 | He et al. |
| RE42,682 E | 9/2011 | Barreras et al. |
| 8,076,807 B2 | 12/2011 | Bohn et al. |
| 8,081,925 B2 | 12/2011 | Parramon et al. |
| 8,096,954 B2 | 1/2012 | Stahmann et al. |
| 8,140,168 B2 | 3/2012 | Olson et al. |
| 8,150,529 B2 | 4/2012 | Snell et al. |
| 8,165,694 B2 | 4/2012 | Carbunaru et al. |
| 8,185,212 B2 | 5/2012 | Carbunaru et al. |
| 8,193,766 B2 | 6/2012 | Rondoni et al. |
| 8,203,434 B2 | 6/2012 | Yoshida |
| 8,244,367 B2 | 8/2012 | Wahlstrand et al. |
| 8,247,926 B2 | 8/2012 | Issa et al. |
| 8,258,653 B2 | 9/2012 | Kitamura et al. |
| 8,265,770 B2 | 9/2012 | Toy et al. |
| 8,278,784 B2 | 10/2012 | Cook et al. |
| 8,292,052 B2 | 10/2012 | Bohori et al. |
| 8,299,652 B2 | 10/2012 | Smith et al. |
| 8,301,079 B2 | 10/2012 | Baarman |
| 8,319,473 B2 | 11/2012 | Choi et al. |
| 8,362,742 B2 | 1/2013 | Kallmyer |
| 8,373,310 B2 | 2/2013 | Baarman et al. |
| 8,378,522 B2 | 2/2013 | Cook et al. |
| 8,378,523 B2 | 2/2013 | Cook et al. |
| 8,463,395 B2 | 6/2013 | Forsell |
| 8,489,200 B2 | 7/2013 | Zarinetchi et al. |
| 8,551,163 B2 | 10/2013 | Aber et al. |
| 8,562,508 B2 | 10/2013 | Dague et al. |
| 8,581,793 B2 | 11/2013 | Carr |
| 8,587,154 B2 | 11/2013 | Fells et al. |
| 8,620,447 B2 | 12/2013 | D'Ambrosio et al. |
| 8,628,460 B2 | 1/2014 | Yomtov et al. |
| 8,629,578 B2 | 1/2014 | Kurs et al. |
| 8,668,473 B2 | 3/2014 | Larose et al. |
| 8,694,117 B2 | 4/2014 | Aghassian et al. |
| 8,810,071 B2 | 8/2014 | Sauerlaender et al. |
| 8,884,468 B2 | 11/2014 | Lemmens et al. |
| 8,909,351 B2 | 12/2014 | Dinsmoor et al. |
| 8,971,958 B2 | 3/2015 | Frikart et al. |
| 9,002,468 B2 | 4/2015 | Shea et al. |
| 9,042,997 B2 * | 5/2015 | Rahman ............... A61N 1/3718 607/60 |
| 9,106,083 B2 | 8/2015 | Partovi |
| 9,192,704 B2 | 11/2015 | Yomtov et al. |
| 9,242,106 B2 * | 1/2016 | Klosterman ......... A61N 1/3605 |

(56) References Cited

U.S. PATENT DOCUMENTS

| | | | |
|---|---|---|---|
| 9,302,093 B2 | 4/2016 | Mashiach | |
| 9,515,494 B2 | 12/2016 | Kurs et al. | |
| 9,515,495 B2 | 12/2016 | Kurs et al. | |
| 9,560,787 B2 | 1/2017 | Kallmyer et al. | |
| 2002/0038138 A1 | 3/2002 | Zarinetchi et al. | |
| 2002/0087204 A1 | 7/2002 | Kung et al. | |
| 2002/0093456 A1 | 7/2002 | Sawamura et al. | |
| 2003/0171792 A1 | 9/2003 | Zarinetchi et al. | |
| 2004/0138725 A1 | 7/2004 | Forsell | |
| 2004/0256146 A1 | 12/2004 | Frericks | |
| 2005/0006083 A1 | 1/2005 | Chen et al. | |
| 2005/0090883 A1 | 4/2005 | Westlund et al. | |
| 2005/0288743 A1 | 12/2005 | Ahn et al. | |
| 2006/0199997 A1 | 9/2006 | Hassler et al. | |
| 2006/0259093 A1 | 11/2006 | Stevenson et al. | |
| 2006/0271129 A1 | 11/2006 | Tai et al. | |
| 2007/0096686 A1 | 5/2007 | Jimenez et al. | |
| 2007/0123948 A1 | 5/2007 | Dal Molin | |
| 2007/0142696 A1 | 6/2007 | Crosby et al. | |
| 2007/0191706 A1 | 8/2007 | Calderon et al. | |
| 2008/0009198 A1 | 1/2008 | Marino | |
| 2008/0027293 A1 | 1/2008 | Vodermayer et al. | |
| 2008/0054638 A1 | 3/2008 | Greene et al. | |
| 2008/0100294 A1 | 5/2008 | Rohling et al. | |
| 2008/0149736 A1 | 6/2008 | Kim et al. | |
| 2008/0167531 A1 | 7/2008 | McDermott | |
| 2008/0211320 A1 | 9/2008 | Cook et al. | |
| 2009/0018616 A1 | 1/2009 | Quick et al. | |
| 2009/0051224 A1 | 2/2009 | Cook et al. | |
| 2009/0072628 A1 | 3/2009 | Cook et al. | |
| 2009/0081943 A1 | 3/2009 | Dobyns et al. | |
| 2009/0174264 A1 | 7/2009 | Onishi et al. | |
| 2009/0212736 A1 | 8/2009 | Baarman et al. | |
| 2009/0226328 A1 | 9/2009 | Morello | |
| 2009/0270679 A1 | 10/2009 | Hoeg et al. | |
| 2009/0284220 A1 | 11/2009 | Toncich et al. | |
| 2010/0019985 A1 | 1/2010 | Bashyam et al. | |
| 2010/0033021 A1 | 2/2010 | Bennett | |
| 2010/0035453 A1 | 2/2010 | Tronnes et al. | |
| 2010/0045114 A1 | 2/2010 | Sample et al. | |
| 2010/0063347 A1 | 3/2010 | Yomtov et al. | |
| 2010/0066305 A1 | 3/2010 | Takahashi et al. | |
| 2010/0069992 A1 | 3/2010 | Aghassian et al. | |
| 2010/0109958 A1 | 5/2010 | Haubrich et al. | |
| 2010/0114143 A1 | 5/2010 | Albrecht et al. | |
| 2010/0122995 A1 | 5/2010 | Thomas et al. | |
| 2010/0171368 A1 | 7/2010 | Schatz et al. | |
| 2010/0184371 A1 | 7/2010 | Cook et al. | |
| 2010/0194334 A1 | 8/2010 | Kirby et al. | |
| 2010/0210233 A1 | 8/2010 | Cook et al. | |
| 2010/0211134 A1 | 8/2010 | Forsell | |
| 2010/0222848 A1 | 9/2010 | Forsell | |
| 2010/0222849 A1 | 9/2010 | Forsell | |
| 2010/0225174 A1 | 9/2010 | Jiang | |
| 2010/0244576 A1 | 9/2010 | Hillan et al. | |
| 2010/0253340 A1 | 10/2010 | Corum et al. | |
| 2010/0256708 A1 | 10/2010 | Thornton et al. | |
| 2010/0277121 A1 | 11/2010 | Hall et al. | |
| 2010/0308939 A1 | 12/2010 | Kurs | |
| 2010/0314946 A1 | 12/2010 | Budde et al. | |
| 2010/0331919 A1 | 12/2010 | Digiore et al. | |
| 2011/0025132 A1 | 2/2011 | Sato | |
| 2011/0043050 A1 | 2/2011 | Yabe et al. | |
| 2011/0046699 A1 | 2/2011 | Mazanec | |
| 2011/0057607 A1 | 3/2011 | Carobolante | |
| 2011/0101790 A1 | 5/2011 | Budgett | |
| 2011/0109263 A1 | 5/2011 | Sakoda et al. | |
| 2011/0115431 A1 | 5/2011 | Dunworth et al. | |
| 2011/0127848 A1 | 6/2011 | Ryu et al. | |
| 2011/0148215 A1 | 6/2011 | Marzetta et al. | |
| 2011/0178361 A1 | 7/2011 | Yomtov | |
| 2011/0181235 A1 | 7/2011 | Walley et al. | |
| 2011/0205083 A1 | 8/2011 | Janna et al. | |
| 2011/0234155 A1 | 9/2011 | Chen et al. | |
| 2011/0241436 A1 | 10/2011 | Furukawa | |
| 2011/0245892 A1 | 10/2011 | Kast et al. | |
| 2011/0266880 A1 | 11/2011 | Kim et al. | |
| 2011/0276110 A1 | 11/2011 | Whitehurst et al. | |
| 2011/0278948 A1 | 11/2011 | Forsell | |
| 2011/0291489 A1 | 12/2011 | Tsai et al. | |
| 2011/0291613 A1 | 12/2011 | Rosik et al. | |
| 2011/0295345 A1 | 12/2011 | Wells et al. | |
| 2011/0298294 A1 | 12/2011 | Takada et al. | |
| 2011/0301667 A1 | 12/2011 | Olson et al. | |
| 2011/0313238 A1 | 12/2011 | Reichenbach et al. | |
| 2012/0001485 A1 | 1/2012 | Uchida | |
| 2012/0032522 A1 | 2/2012 | Schatz et al. | |
| 2012/0039102 A1 | 2/2012 | Shinoda | |
| 2012/0057322 A1 | 3/2012 | Waffenschmidt | |
| 2012/0065458 A1 | 3/2012 | Tol | |
| 2012/0080957 A1 | 4/2012 | Cooper et al. | |
| 2012/0091951 A1 | 4/2012 | Sohn | |
| 2012/0104997 A1 | 5/2012 | Carobolante | |
| 2012/0109256 A1 | 5/2012 | Meskins et al. | |
| 2012/0119914 A1 | 5/2012 | Uchida | |
| 2012/0146575 A1 | 6/2012 | Armstrong et al. | |
| 2012/0149229 A1 | 6/2012 | Kearsley et al. | |
| 2012/0150259 A1 | 6/2012 | Meskens | |
| 2012/0153739 A1 | 6/2012 | Cooper et al. | |
| 2012/0153954 A1 | 6/2012 | Ota et al. | |
| 2012/0157753 A1 | 6/2012 | D'Ambrosio | |
| 2012/0157754 A1 | 6/2012 | D'Ambrosio | |
| 2012/0158407 A1 | 6/2012 | Forsell | |
| 2012/0161539 A1 | 6/2012 | Kim et al. | |
| 2012/0164943 A1 | 6/2012 | Bennett | |
| 2012/0169132 A1 | 7/2012 | Choudhary et al. | |
| 2012/0169133 A1 | 7/2012 | Lisi et al. | |
| 2012/0169137 A1 | 7/2012 | Lisi et al. | |
| 2012/0169139 A1 | 7/2012 | Kudo | |
| 2012/0169278 A1 | 7/2012 | Choi et al. | |
| 2012/0175967 A1 | 7/2012 | Dibben et al. | |
| 2012/0235364 A1 | 9/2012 | Wang et al. | |
| 2012/0239118 A1 | 9/2012 | Ozawa et al. | |
| 2012/0245649 A1 | 9/2012 | Bohori et al. | |
| 2012/0245664 A1 | 9/2012 | Smith et al. | |
| 2012/0259398 A1 | 10/2012 | Chen et al. | |
| 2012/0274148 A1 | 11/2012 | Sung et al. | |
| 2012/0306433 A1 | 12/2012 | Kim et al. | |
| 2013/0007949 A1 | 1/2013 | Kurs et al. | |
| 2013/0060103 A1 | 3/2013 | Bergida et al. | |
| 2013/0119773 A1 | 5/2013 | Davis | |
| 2013/0127253 A1 | 5/2013 | Stark et al. | |
| 2013/0149960 A1 | 6/2013 | Dec et al. | |
| 2013/0159956 A1 | 6/2013 | Verghese et al. | |
| 2013/0190551 A1 | 7/2013 | Callaway et al. | |
| 2013/0197607 A1 | 8/2013 | Wilder et al. | |
| 2013/0214731 A1 | 8/2013 | Dinsmoor | |
| 2013/0241306 A1 | 9/2013 | Aber et al. | |
| 2013/0241468 A1 | 9/2013 | Moshfeghi | |
| 2013/0271088 A1 | 10/2013 | Hwang et al. | |
| 2013/0289334 A1 | 10/2013 | Badstibner et al. | |
| 2013/0310630 A1 | 11/2013 | Smith et al. | |
| 2013/0320773 A1 | 12/2013 | Schatz et al. | |
| 2013/0331638 A1 | 12/2013 | Cameron et al. | |
| 2014/0005466 A1 | 1/2014 | Crosby et al. | |
| 2014/0008446 A1* | 1/2014 | Carr | H01Q 1/248 235/492 |
| 2014/0011447 A1 | 1/2014 | Konanur et al. | |
| 2014/0028110 A1 | 1/2014 | Petersen et al. | |
| 2014/0028111 A1 | 1/2014 | Hansen et al. | |
| 2014/0031606 A1 | 1/2014 | Hansen et al. | |
| 2014/0125141 A1* | 5/2014 | Shinohe | H01Q 1/2266 307/104 |
| 2014/0152252 A1 | 6/2014 | Wood | |
| 2014/0163644 A1 | 6/2014 | Scott et al. | |
| 2014/0265620 A1 | 9/2014 | Hoarau et al. | |
| 2014/0265621 A1 | 9/2014 | Wong et al. | |
| 2014/0275727 A1 | 9/2014 | Bonde et al. | |
| 2015/0123654 A1 | 5/2015 | Gagnon et al. | |
| 2015/0207330 A1 | 7/2015 | Petersen | |
| 2015/0207331 A1 | 7/2015 | Petersen | |
| 2015/0222127 A1 | 8/2015 | Hansen | |
| 2015/0222128 A1 | 8/2015 | Hansen | |
| 2015/0222139 A1 | 8/2015 | Petersen et al. | |

(56) References Cited

U.S. PATENT DOCUMENTS

| | | |
|---|---|---|
| 2015/0229289 A1 | 8/2015 | Suzuki |
| 2015/0290373 A1 | 10/2015 | Rudser et al. |
| 2016/0135684 A1 | 5/2016 | Kappel et al. |
| 2016/0218432 A1 | 7/2016 | Pope et al. |
| 2016/0250484 A1 | 9/2016 | Nguyen et al. |
| 2016/0254703 A1 | 9/2016 | Hansen |
| 2016/0254704 A1 | 9/2016 | Hansen et al. |

FOREIGN PATENT DOCUMENTS

| | | |
|---|---|---|
| EP | 0589608 A2 | 9/1993 |
| EP | 1513241 A1 | 3/2005 |
| EP | 2267864 A2 | 6/2010 |
| GB | 2477034 A | 7/2011 |
| JP | H03109063 A | 5/1991 |
| JP | 11-506646 | 6/1999 |
| JP | 2013094456 A | 5/2013 |
| JP | 2013161640 A | 8/2013 |
| JP | 2014160611 A | 9/2014 |
| KR | 1020020089605 | 11/2002 |
| KR | 1020120007296 | 1/2012 |
| KR | 1020120077448 | 7/2012 |
| WO | 0001442 A2 | 1/2000 |
| WO | 0074747 A1 | 12/2000 |
| WO | 0137926 A1 | 5/2001 |
| WO | 2005106901 A2 | 11/2005 |
| WO | 2007053881 A1 | 5/2007 |
| WO | 2007084510 A1 | 7/2007 |
| WO | 2008066941 A2 | 6/2008 |
| WO | 2009018271 A1 | 2/2009 |
| WO | 2009021220 A1 | 2/2009 |
| WO | 2009023905 A1 | 2/2009 |
| WO | 2009042977 A1 | 4/2009 |
| WO | 2010030378 A1 | 3/2010 |
| WO | 2010089354 A2 | 8/2010 |
| WO | 2011081626 A1 | 7/2011 |
| WO | 2011113934 A1 | 9/2011 |
| WO | 2012002063 A1 | 1/2012 |
| WO | 2012056365 A2 | 5/2012 |
| WO | 2012087807 A2 | 6/2012 |
| WO | 2012087811 A2 | 6/2012 |
| WO | 2012087816 A2 | 6/2012 |
| WO | 2012087819 A2 | 6/2012 |
| WO | 2012099965 A2 | 7/2012 |
| WO | 2012141752 A2 | 10/2012 |
| WO | 2013110602 A1 | 8/2013 |
| WO | 2013138451 A1 | 9/2013 |
| WO | 2014039673 A1 | 3/2014 |

OTHER PUBLICATIONS

Merli, Francesco, et al., "Design, Realization and Measurements of a Miniature Antenna for Implantable Wireless Communication Systems", IEEE Transaction on Antennas and Propagation, vol. 59, No. 10, Oct. 2011, pp. 3544-3555.

Merli, Francesco, et al.,"The Effect of Insulating Layers on the Performance of Implanted Antennas", IEEE Transaction on Antennas and Propagation, vol. 59, No. 1, Jan. 2011, pp. 21-31.

Abadia, Javier, et al., 3D-Spiral Small Antenna Design and Realization for Biomdical Telemetry in the MICS Band. Radioengineering, vol. 18, No. 4, Dec. 2009, pp. 359-367.

Bonde et al.; Promise of unrestricted mobility with innovative, portable wireless powering of a mechanical circulatory assist device; American Association for Thoracic Surgery; © 2012; 2 pgs.; retrieved Mar. 12, 2014 from the internet: http://aats.org/annualmeeting/Abstracts/2012/T8.cgi.

Chargepoint, Inc.; −chargepoin+®; product brochure; 4 pgs.; © 2014; retrieved Mar. 12, 2014 from the internet: http://www.chargepoint.com/network/.

Dixon, Jr.; Eddy current losses in transformer windings and circuit wiring; Unitrode Corp. Seminar Manual (SEM600); Watertown, MA; 12 pgs.; 1988 (year of pub. sufficiently earlier than effective US filing date and any foreign priority date).

Evatran; PluglessTM Level 2 EV Charging System (3.3kW); product brochure; 7 pgs.; retrieved Mar. 12, 2014 from the internet: http://www.pluglesspower.com/tech-specs/.

Ferret, B.; Electric vehicles get big boost!; Renewable Energy World; 3 pgs.; Jul. 30, 2012; retrieved Jul. 30, 2012 from the internet: http://www.renewableenergyworld.com/rea/blog/post/2012/07/.

Motavalli, Jim; WiTricity Takes Its Car-Charging Technology Out for a Road Test; New York Times; 3 pgs.; Jul. 25, 2012; retrieved Mar. 12, 2014 from the internet: http://wheels.blogs.nytimes.com/2012/07/25/witricity-takes-its-car-charging-technology-out-for-a-road-test/.

Notification of Transmittal of the International Search Report and the Written Opinion of the International Searching Authority for PCT Application No. PCT/US2015/051474, dated Dec. 30, 2015.

Qing X et al: "Segmented loop antenna for UHF near-field RFID applications", Electronic Let, The Institution of Engineering and Technology, vol. 45, No. 17, Aug. 13, 2009 (Aug. 13, 2009), pp. 872-873.

Xianming Qing et al: "A Broadband UHF Near-Field RFID Antenna", IEEE Transactions on Antennas and Propagation, vol. 58, No. 12, Sep. 23, 2010 (Sep. 23, 2010), pp. 3829-3838.

European Search Report issued in EP Patent Application No. 15843159.3, dated Apr. 25, 2018, 11 pages.

* cited by examiner

ANTENNA DESIGNS FOR
COMMUNICATION BETWEEN A
WIRELESSLY POWERED IMPLANT TO AN
EXTERNAL DEVICE OUTSIDE THE BODY

CROSS-REFERENCE TO RELATED
APPLICATIONS

This application claims the benefit of U.S. Provisional Appln. No. 62/053,663, titled "Antenna Designs for Communication Between a Wirelessly Powered Implant to an External Device Outside the Body", filed Sep. 22, 2014, which is incorporated herein by reference in its entirety.

INCORPORATION BY REFERENCE

All publications and patent applications mentioned in this specification are herein incorporated by reference to the same extent as if each individual publication or patent application was specifically and individually indicated to be incorporated by reference.

FIELD

The field relates generally to resonant wireless power transfer systems, and more specifically to communication systems and methods for implantable resonant wireless power transfer systems.

BACKGROUND

Many types of devices require transmitting energy between locations. Recent advances have accelerated the pace of innovation for wireless energy transmission (WET) without the use of cords. An example of a system using wireless energy technology is a powered, implantable medical device.

Many implantable medical devices require electrical systems to power the implant. Typically, this is achieved using percutaneous wiring to connect a power source to the implant. More recently, there has been interest in development of Transcutaneous Energy Transfer (TET) systems, e.g., through an oscillating magnetic field, for powering implantable medical devices.

A TET system usually includes a number of components or systems. A conventional TET system is implemented with a transmitting coil and a receiving coil for transmitting energy across the skin layer. The system typically includes a controller for driving the transmitting coil and/or controlling the implanted electronics.

Typically, implantable medical devices, such as implanted sensors, require very little power to operate. With such low power levels (on the order of milliwatts), power transfer levels and efficiency can be lower. With higher power devices (e.g., on the order of watts and up to 15 W or more), efficient transfer of wireless power is extremely important. Additionally, positions within the body are limited that can accommodate larger implanted devices, some of which are deep below the skin surface. These implant locations require additional attention to position and orientation of both the transmit and receive coils, as well as techniques to improve and maximize transfer efficiency.

Previous TET systems for implantable medical devices required the implanted receiver coil to be positioned just under the skin, and typically include a mechanical feature to align the receive and transmit coils and keep them together. By implanting these devices directly under the skin, the size and power requirements of these implanted devices is limited if they are to be powered by a TET system. TET systems can be designed for operation even while power is not being received by the receiver coil. In a typical configuration, solid-state electronics and a battery can power the implanted medical device when external power is interrupted or not available. In this case, it may be beneficial to provide a user interface or other electronic device to communicate information to the patient and/or caregiver regarding the implanted components. For example, a user interface may include alarms to notify the patient when the internal battery level is low.

Reliable communication between an implantable medical device, a user interface, and an external transmitter can be a challenge because of varying conditions and distances between the components of the TET system.

Radio signals have limitations when used for communication between implantable devices. Attenuation of radio signals by the human body is very large and can disrupt communication signals. Even under optimal circumstances, such as a shallow implant depth, a properly designed antenna, proper orientation of the implanted module, and a reliable radio link, attenuation can be on the order of 10 dB to 20 dB. For deeper implant depths, or if the implant rotates significantly from its intended position, attenuation may grow to 100 dB or more. This can lead to an unreliable or totally interrupted radio link with a high loss rate.

In-band communication has been used in implanted systems and comprises modulation of a receiver load that can be sensed by a transmitter. The problem with in-band communication is that it requires additional electronics in the resonant circuit, which lowers the power transfer efficiency and leads to additional heating of the receiver. Additionally, there is a fundamental design conflict between optimizing a resonant circuit to be power efficient and to transmit a meaningful amount of information. The former requires coils with a high quality factor while the latter prefers lower quality factors.

It is therefore desirable to provide a system in which the implant can communicate effectively with the user interface in the absence of the transmitter.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

SUMMARY OF THE DISCLOSURE

Figure 1:
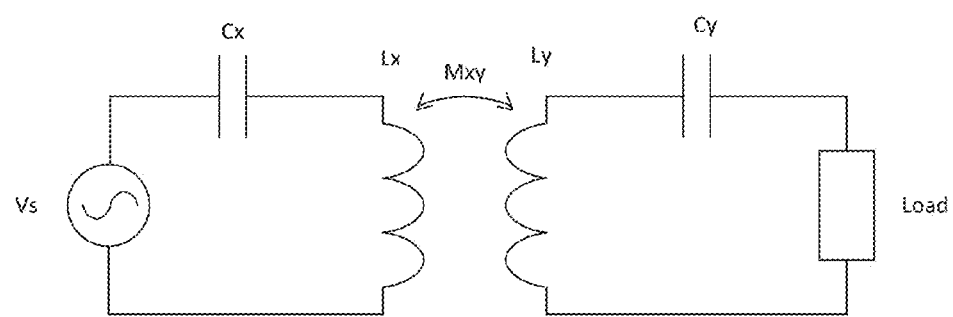
FIG. 1 illustrates a basic wireless power transfer system.

An antenna for use in a wireless power system is provided, comprising a differential transmission line, a plurality of conductive elements coupled to the differential transmission line and configured to radiate RF energy to transmit and receive radio information, and a plurality of gaps positioned between adjacent conductive elements, the gaps being configured to prevent or reduce induction of current in the plurality of conductive elements when the antenna is exposed to a magnetic field.

In some embodiments, the plurality of conductive elements are arranged so as to provide a first electrical path and a second electrical path. In other embodiments, the first electrical path comprises an interior trace of the antenna, and the second electrical path comprises an exterior trace of the antenna. In another embodiment, the first electrical path is tuned to a first resonant frequency, and the second electrical path is tuned to a second resonant frequency.

A wireless receiver for use in a TET system is provided, comprising a hermetic internal housing, an energy source disposed in the internal housing, a controller disposed in the housing, the controller configured to control operation of the TET receiver, a low-frequency ferrite housing disposed around the internal housing, the ferrite housing configured to reduce the amount of magnetic flux that reaches the internal housing, at least one wire coil wrapped around the ferrite housing, the at least one wire coil configured to receive wireless energy from an external power transmitter, an antenna body, a plurality of conductive elements disposed on the antenna body, a differential transmission line electrically connecting the plurality of conductive elements to the controller and configured to deliver RF energy to the plurality of conductive elements to transmit and receive radio information, and a plurality of gaps positioned between adjacent conductive elements, the gaps being configured to prevent or reduce induction of current in the plurality of conductive elements when the antenna is exposed to a magnetic field.

In some embodiments, the plurality of conductive elements are arranged so as to provide a first electrical path and a second electrical path. In other embodiments, the first electrical path comprises an interior trace of the antenna, and the second electrical path comprises an exterior trace of the antenna. In another embodiment, the first electrical path is tuned to a first resonant frequency, and the second electrical path is tuned to a second resonant frequency.

In one embodiment, the receiver further comprises a high-frequency ferrite material positioned between the plurality of conductive elements and the low-frequency ferrite material.

An implantable antenna assembly for communicating with an external device is provided, comprising a housing formed of metal for enclosing electrical elements, a low-frequency ferrite layer disposed on an outer surface of the housing, an antenna body disposed over the low-frequency ferrite layer, and an antenna metal disposed on the antenna body.

In some embodiments, the antenna metal is a resonant structure formed of metal strips.

In one embodiment, the metal strips are formed in a pattern having a region of symmetry.

In one embodiment, the antenna further comprises a high-frequency ferrite layer disposed between the low-frequency ferrite layer and the antenna body.

In another embodiment, the antenna further comprises a conductive well extending from within the housing to the antenna metal. In one embodiment, the conductive well comprises the feedthrough pins formed within a ceramic.

In some embodiments, the antenna further comprises feedthrough pins extending from within the housing to the antenna metal.

In one embodiment, the antenna further comprises a clearance layer separating the high-frequency ferrite layer from the housing.

In some embodiments, the antenna assembly does not include a ground plane.

A communications antenna is provided, comprising a differential transmission line, a plurality of conductive elements coupled to the differential transmission line and configured to radiate RF energy to transmit and receive radio information, and a plurality of gaps positioned between adjacent conductive elements, the gaps being configured to prevent or reduce induction of current in the plurality of conductive elements when the antenna is exposed to a magnetic field.

DETAILED DESCRIPTION

In the description that follows, like components have been given the same reference numerals, regardless of whether they are shown in different embodiments. To illustrate an embodiment(s) of the present disclosure in a clear and concise manner, the drawings may not necessarily be to scale and certain features may be shown in somewhat schematic form. Features that are described and/or illustrated with respect to one embodiment may be used in the same way or in a similar way in one or more other embodiments and/or in combination with or instead of the features of the other embodiments.

Various aspects of the invention are similar to those described in International Patent Pub. No. WO2012045050; U.S. Pat. Nos. 8,140,168; 7,865,245; 7,774,069; 7,711,433; 7,650,187; 7,571,007; 7,741,734; 7,825,543; 6,591,139; 6,553,263; and 5,350,413; and U.S. Pub. Nos. 2010/0308939; 2008/027293; and 2010/0102639, the entire contents of which patents and applications are incorporated herein for all purposes.

Wireless Power Transmission System

Power may be transmitted wirelessly by magnetic induction. In various embodiments, the transmitter and receiver are closely coupled.

In some cases "closely coupled" or "close coupling" refers to a system that requires the coils to be very near each other in order to operate. In some cases "loosely coupled" or "loose coupling" refers to a system configured to operate when the coils have a significant spatial and/or axial separation, and in some cases up to distance equal to or less than the diameter of the larger of the coils. In some cases, "loosely coupled" or "loose coupling" refers a system that is relatively insensitive to changes in physical separation and/or orientation of the receiver and transmitter.

In some cases "loosely coupled" or "loose coupling" refers to a system configured to operate when the coils have a significant spatial and/or axial separation, and in some cases up to distance equal to or less than the diameter of the larger of the coils. In some cases, "loosely coupled" or "loose coupling" refers a system that is relatively insensitive to changes in physical separation and/or orientation of the receiver and transmitter. In some cases, "loosely coupled" or "loose coupling" refers a highly resonant system and/or a system using strongly-coupled magnetic resonators.

In various embodiments, the transmitter and receiver are non-resonant coils. For example, a change in current in one coil induces a changing magnetic field. The second coil within the magnetic field picks up the magnetic flux, which in turn induces a current in the second coil. An example of a closely coupled system with non-resonant coils is described in International Pub. No. WO2000/074747, incorporated herein for all purposes by reference. A conventional transformer is another example of a closely coupled, non-resonant system. In various embodiments, the transmitter and receiver are resonant coils. For example, one or both of the coils is connected to a tuning capacitor or other means for controlling the frequency in the respective coil. Examples of closely coupled system with resonant coils are described in International Pub. Nos. WO2001/037926; WO2012/087807; WO2012/087811; WO2012/087816; WO2012/087819; WO2010/030378; and WO2012/056365, U.S. Pub. No. 2003/0171792, and U.S. Pat. No. 5,350,413 (now abandoned), incorporated herein for all purposes by reference.

For given coil sizes and separations, coupling a given amount of power requires generating the same magnetic field strength for either inductive or resonant systems. This requires the same number of ampere-turns in the coils. In inductive systems, all the ampere-turns pass through the MOSFETs and generate power losses in their on-state resistance. In resonant systems, only the exciter ampere-turns pass through the MOSFETs, while the resonator ampere-turns do not. As a consequence, resonant systems will always have lower losses and higher efficiencies than inductive systems of the same dimensions and power through-put.

In various embodiments, the transmitter and receiver are non-resonant coils. For example, a change in current in one coil induces a changing magnetic field. The second coil within the magnetic field picks up the magnetic flux, which in turn induces a current in the second coil. An example of a closely coupled system with non-resonant coils is described in International Pub. No. WO2000/074747, incorporated herein for all purposes by reference. A conventional transformer is another example of a closely coupled, non-resonant system. In various embodiments, the transmitter and receiver are resonant coils. For example, one or both of the coils is connected to a tuning capacitor or other means for controlling the frequency in the respective coil. An example of closely coupled system with resonant coils is described in International Pub. Nos. WO2001/037926; WO2012/087807; WO2012/087811; WO2012/087816; WO2012/087819; WO2010/030378; and WO2012/056365, and U.S. Pub. No. 2003/0171792, incorporated herein for all purposes by reference.

In various embodiments, the transmitter and receiver are loosely coupled. For example, the transmitter can resonate to propagate magnetic flux that is picked up by the receiver at relatively great distances. In some cases energy can be transmitted over several meters. In a loosely coupled system power transfer may not necessarily depend on a critical distance. Rather, the system may be able to accommodate changes to the coupling coefficient between the transmitter and receiver. An example of a loosely coupled system is described in International Pub. No. WO2012/045050, incorporated herein for all purposes by reference.

Power may be transmitted wirelessly by radiating energy. In various embodiments, the system comprises antennas. The antennas may be resonant or non-resonant. For example, non-resonant antennas may radiate electromagnetic waves to create a field. The field can be near field or far field. The field can be directional. Generally far field has greater range but a lower power transfer rate. An example of such a system for radiating energy with resonators is described in International Pub. No. WO2010/089354, incorporated herein for all purposes by reference. An example of such a non-resonant system is described in International Pub. No. WO2009/018271, incorporated herein for all purposes by reference. Instead of antenna, the system may comprise a high energy light source such as a laser. The system can be configured so photons carry electromagnetic energy in a spatially restricted, direct, coherent path from a transmission point to a receiving point. An example of such a system is described in International Pub. No. WO2010/089354, incorporated herein for all purposes by reference.

Power may also be transmitted by taking advantage of the material or medium through which the energy passes. For example, volume conduction involves transmitting electrical energy through tissue between a transmitting point and a receiving point. An example of such a system is described in International Pub. No. WO2008/066941, incorporated herein for all purposes by reference.

Power may also be transferred using a capacitor charging technique. The system can be resonant or non-resonant. Exemplars of capacitor charging for wireless energy transfer are described in International Pub. No. WO2012/056365, incorporated herein for all purposes by reference.

The system in accordance with various aspects of the invention will now be described in connection with a system for wireless energy transfer by magnetic induction. The exemplary system utilizes resonant power transfer. The system works by transmitting power between the two inductively coupled coils. In contrast to a transformer, however, the exemplary coils are not coupled together closely. A transformer generally requires the coils to be aligned and positioned directly adjacent each other. The exemplary system accommodates looser coupling of the coils.

While described in terms of one receiver coil and one transmitter coil, one will appreciate from the description herein that the system may use two or more receiver coils and two or more transmitter coils. For example, the transmitter may be configured with two coils—a first coil to resonate flux and a second coil to excite the first coil. One will further appreciate from the description herein that usage of "resonator" and "coil" may be used somewhat interchangeably. In various respects, "resonator" refers to a coil and a capacitor connected together.

In accordance with various embodiments of this disclosure, the system comprises one or more transmitters configured to transmit power wirelessly to one or more receivers. In various embodiments, the system includes a transmitter and more than one receiver in a multiplexed arrangement. A frequency generator may be electrically coupled to the transmitter to drive the transmitter to transmit power at a particular frequency or range of frequencies. The frequency generator can include a voltage controlled oscillator and one or more switchable arrays of capacitors, a voltage controlled oscillator and one or more varactors, a phase-locked-loop, a direct digital synthesizer, or combinations thereof. The transmitter can be configured to transmit power at multiple frequencies simultaneously. The frequency generator can include two or more phase-locked-loops electrically coupled to a common reference oscillator, two or more independent voltage controlled oscillators, or combinations thereof. The transmitter can be arranged to simultaneously delivery power to multiple receivers at a common frequency.

In various embodiments, the transmitter is configured to transmit a low power signal at a particular frequency. The transmitter may transmit the low power signal for a particular time and/or interval. In various embodiments, the transmitter is configured to transmit a high power signal wirelessly at a particular frequency. The transmitter may transmit the high power signal for a particular time and/or interval.

In various embodiments, the receiver includes a frequency selection mechanism electrically coupled to the receiver coil and arranged to allow the resonator to change a frequency or a range of frequencies that the receiver can receive. The frequency selection mechanism can include a switchable array of discrete capacitors, a variable capacitance, one or more inductors electrically coupled to the receiving antenna, additional turns of a coil of the receiving antenna, or combinations thereof.

In general, most of the flux from the transmitter coil does not reach the receiver coil. The amount of flux generated by the transmitter coil that reaches the receiver coil is described by "k" and referred to as the "coupling coefficient."

In various embodiments, the system is configured to maintain a value of k in the range of between about 0.2 to about 0.01. In various embodiments, the system is configured to maintain a value of k of at least 0.01, at least 0.02, at least 0.03, at least 0.04, or at least 0.05.

In various embodiments, the coils are physically separated. In various embodiments, the separation is greater than a thickness of the receiver coil. In various embodiments, the separation distance is equal to or less than the diameter of the larger of the receiver and transmitter coil.

Because most of the flux does not reach the receiver, the transmitter coil must generate a much larger field than what is coupled to the receiver. In various embodiments, this is accomplished by configuring the transmitter with a large number of amp-turns in the coil.

Since only the flux coupled to the receiver gets coupled to a real load, most of the energy in the field is reactive. The current in the coil can be sustained with a capacitor connected to the coil to create a resonator. The power source thus only needs to supply the energy absorbed by the receiver. The resonant capacitor maintains the excess flux that is not coupled to the receiver.

In various embodiments, the impedance of the receiver is matched to the transmitter. This allows efficient transfer of energy out of the receiver. In this case the receiver coil may not need to have a resonant capacitor.

Turning now to FIG. 1, a simplified circuit for wireless energy transmission is shown. The exemplary system shows a series connection, but the system can be connected as either series or parallel on either the transmitter or receiver side.

The exemplary transmitter includes a coil Lx connected to a power source Vs by a capacitor Cx. The exemplary receiver includes a coil Ly connected to a load by a capacitor Cy. Capacitor Cx may be configured to make Lx resonate at a desired frequency. Capacitance Cx of the transmitter coil may be defined by its geometry. Inductors Lx and Ly are connected by coupling coefficient k. Mxy is the mutual inductance between the two coils. The mutual inductance, Mxy, is related to coupling coefficient, k.

$$Mxy = k\sqrt{Lx \cdot Ly}$$

In the exemplary system the power source Vs is in series with the transmitter coil Lx so it may have to carry all the reactive current. This puts a larger burden on the current rating of the power source and any resistance in the source will add to losses.

The exemplary system includes a receiver configured to receive energy wirelessly transmitted by the transmitter. The exemplary receiver is connected to a load. The receiver and load may be connected electrically with a controllable switch.

In various embodiments, the receiver includes a circuit element configured to be connected or disconnected from the receiver coil by an electronically controllable switch. The electrical coupling can include both a serial and parallel arrangement. The circuit element can include a resistor, capacitor, inductor, lengths of an antenna structure, or combinations thereof. The system can be configured such that power is transmitted by the transmitter and can be received by the receiver in predetermined time increments.

In various embodiments, the transmitter coil and/or the receiver coil is a substantially two-dimensional structure. In various embodiments, the transmitter coil may be coupled to a transmitter impedance-matching structure. Similarly, the receiver coil may be coupled to a receiver impedance-matching structure. Examples of suitable impedance-matching structures include, but are not limited to, a coil, a loop, a transformer, and/or any impedance-matching network. An impedance-matching network may include inductors or capacitors configured to connect a signal source to the resonator structure.

In various embodiments, the transmitter is controlled by a controller (not shown) and driving circuit. The controller and/or driving circuit may include a directional coupler, a signal generator, and/or an amplifier. The controller may be configured to adjust the transmitter frequency or amplifier gain to compensate for changes to the coupling between the receiver and transmitter.

In various embodiments, the transmitter coil is connected to an impedance-matched coil loop. The loop is connected to a power source and is configured to excite the transmitter coil. The first coil loop may have finite output impedance. A signal generator output may be amplified and fed to the transmitter coil. In use power is transferred magnetically between the first coil loop and the main transmitter coil, which in turns transmits flux to the receiver. Energy received by the receiver coil is delivered by Ohmic connection to the load.

One of the challenges to a practical circuit is how to get energy in and out of the resonators. Simply putting the power source and load in series or parallel with the resonators is difficult because of the voltage and current required. In various embodiments, the system is configured to achieve an approximate energy balance by analyzing the system characteristics, estimating voltages and currents involved, and controlling circuit elements to deliver the power needed by the receiver.

In an exemplary embodiment, the system load power, $P_L$, is assumed to be 15 Watts and the operating frequency of the system, f, is 250 kHz. Then, for each cycle the load removes a certain amount of energy from the resonance:

$$e_L = \frac{P_L}{f} = 60 \ \mu J \quad \text{Energy the load removes in one cycle}$$

It has been found that the energy in the receiver resonance is typically several times larger than the energy removed by the load for operative, implantable medical devices. In various embodiments, the system assumes a ratio 7:1 for energy at the receiver versus the load removed. Under this assumption, the instantaneous energy in the exemplary receiver resonance is 420 µJ.

The exemplary circuit was analyzed and the self inductance of the receiver coil was found to be 60 uH. From the energy and the inductance, the voltage and current in the resonator could be calculated.

$$e_y = \frac{1}{2}Li^2$$

$$i_y = \sqrt{\frac{2e_y}{L}} = 3.74 \text{ A peak}$$

$$v_y = \omega L_y i_y = 352 \text{ V peak}$$

The voltage and current can be traded off against each other. The inductor may couple the same amount of flux regardless of the number of turns. The Amp-turns of the coil needs to stay the same in this example, so more turns means the current is reduced. The coil voltage, however, will need to increase. Likewise, the voltage can be reduced at the expense of a higher current. The transmitter coil needs to have much more flux. The transmitter flux is related to the receiver flux by the coupling coefficient. Accordingly, the energy in the field from the transmitter coil is scaled by k.

$$e_x = \frac{e_y}{k}$$

Given that k is 0.05:

$$e_x = \frac{420 \text{ µJ}}{0.05} = 8.4 \text{ mJ}$$

For the same circuit the self inductance of the transmitter coil was 146 uH as mentioned above. This results in:

$$i_x = \sqrt{\frac{2e_x}{L}} = 10.7 \text{ A peak}$$

$$v_x = \omega L_x i_x = 2460 \text{ V peak}$$

One can appreciate from this example, the competing factors and how to balance voltage, current, and inductance to suit the circumstance and achieve the desired outcome. Like the receiver, the voltage and current can be traded off against each other. In this example, the voltages and currents in the system are relatively high. One can adjust the tuning to lower the voltage and/or current at the receiver if the load is lower.

Estimation of Coupling Coefficient and Mutual Inductance

As explained above, the coupling coefficient, k, may be useful for a number of reasons. In one example, the coupling coefficient can be used to understand the arrangement of the coils relative to each other so tuning adjustments can be made to ensure adequate performance. If the receiver coil moves away from the transmitter coil, the mutual inductance will decrease, and ceteris paribus, less power will be transferred. In various embodiments, the system is configured to make tuning adjustments to compensate for the drop in coupling efficiency.

The exemplary system described above often has imperfect information. For various reasons as would be understood by one of skill in the art, the system does not collect data for all parameters. Moreover, because of the physical gap between coils and without an external means of communications between the two resonators, the transmitter may have information that the receiver does not have and vice versa. These limitations make it difficult to directly measure and derive the coupling coefficient, k, in real time.

Described below are several principles for estimating the coupling coefficient, k, for two coils of a given geometry. The approaches may make use of techniques such as Biot-Savart calculations or finite element methods. Certain assumptions and generalizations, based on how the coils interact in specific orientations, are made for the sake of simplicity of understanding. From an electric circuit point of view, all the physical geometry permutations can generally lead to the coupling coefficient.

Figure 2:
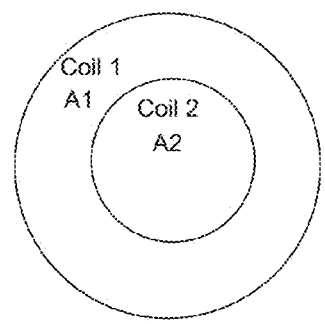
FIG. 2 illustrates the flux generated by a pair of coils.

If two coils are arranged so they are in the same plane, with one coil circumscribing the other, then the coupling coefficient can be estimated to be roughly proportional to the ratio of the area of the two coils. This assumes the flux generated by coil 1 is roughly uniform over the area it encloses as shown in FIG. 2.

Figure 3A:
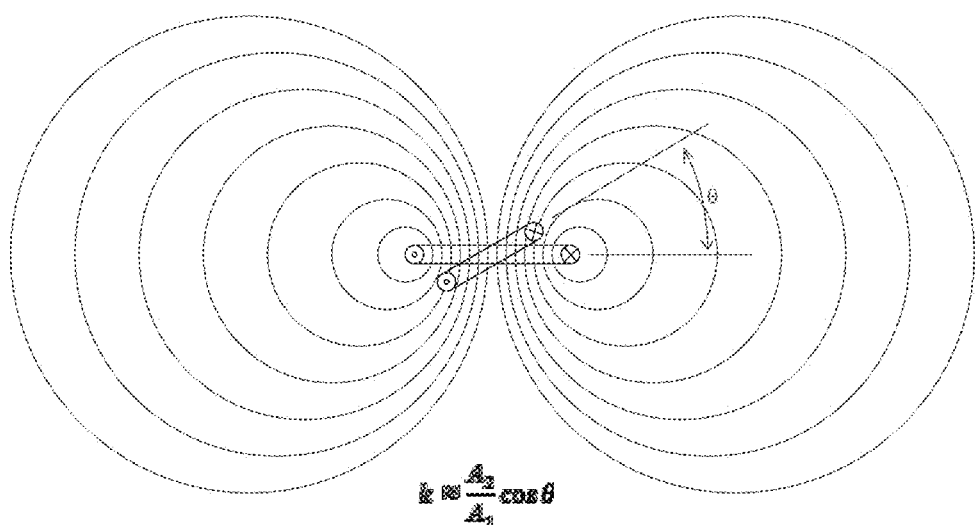
FIGS. 3A-3B illustrate the effect of coil alignment on the coupling coefficient.

If the coils are out of alignment such that the coils are at a relative angle, the coupling coefficient will decrease. The amount of the decrease is estimated to be about equal to the cosine of the angle as shown in FIG. 3A. If the coils are orthogonal to each other such that theta (θ) is 90 degrees, the flux will not be received by the receiver and the coupling coefficient will be zero.

Figure 3B:
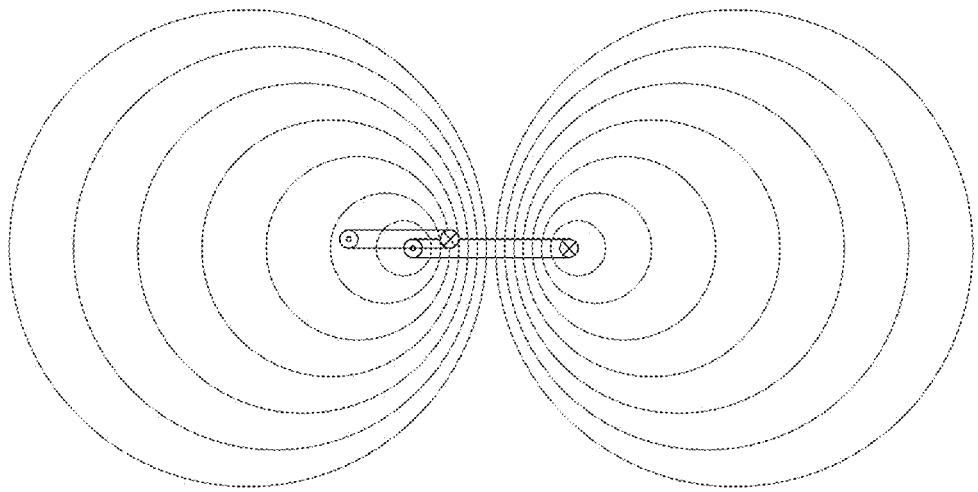

If the coils are arraigned such that half the flux from one coil is in one direction and the other half is in the other direction, the flux cancels out and the coupling coefficient is zero, as shown in FIG. 3B.

A final principle relies on symmetry of the coils. The coupling coefficient and mutual inductance from one coil to the other is assumed to be the same regardless of which coil is being energized.

$$M_{xy}=M_{yx}$$

Figure 4:
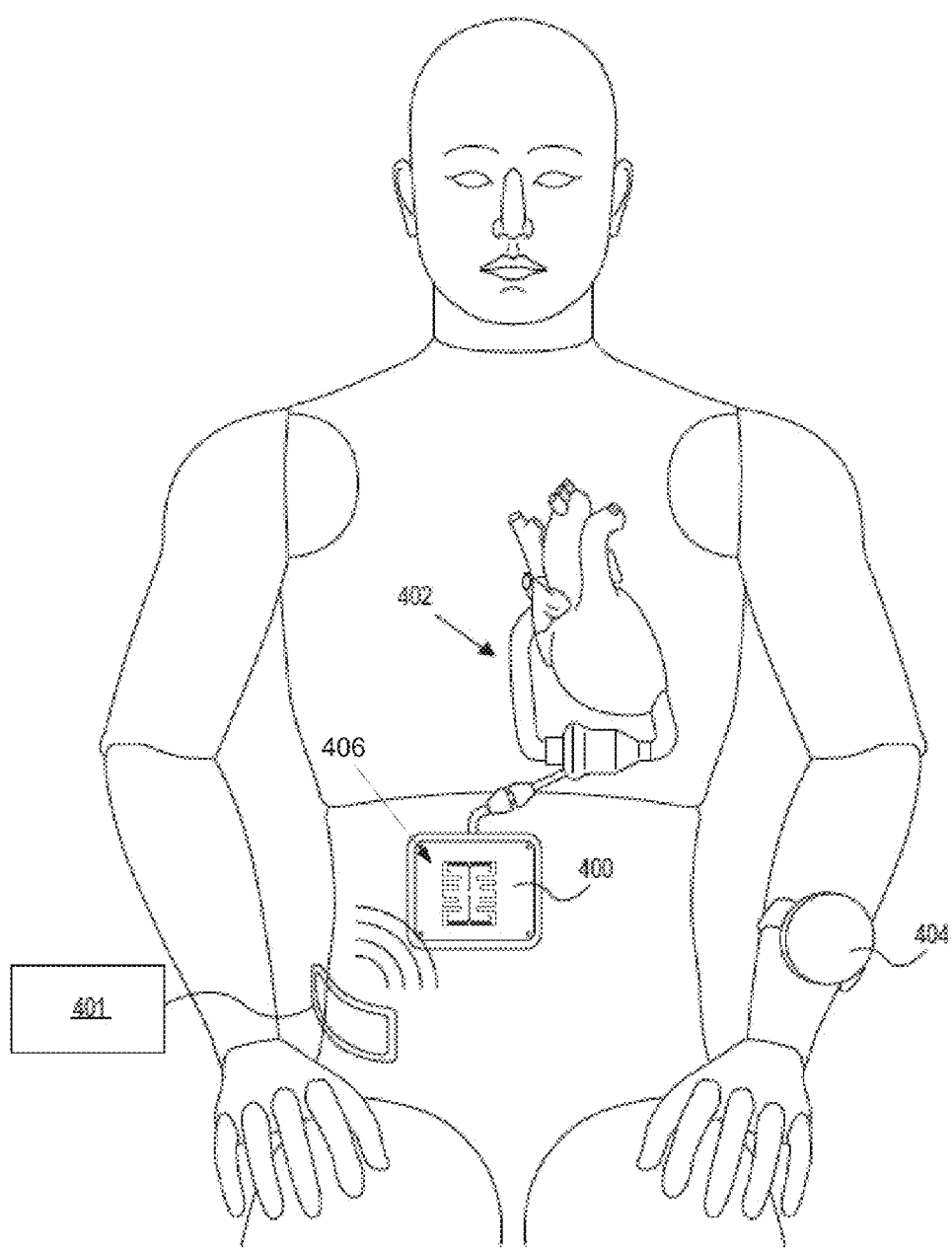
FIG. 4 is one embodiment of a wireless power transfer system including a communications antenna on an implantable TETS receiver.

FIG. 4 illustrates a wireless power transfer system comprising an implantable TETS receiver unit 400 implanted in an abdomen of a human patient. The receiver unit 400 can be coupled to a device load 402, such as an implantable medical device, e.g., an implantable LVAD or heart pump. The exemplary receiver unit 400 can include a receiver resonator coil and electronics configured to receive wireless energy from an external transmitter 401, which can include a power supply such as a pulse generator connected to a transmitter resonator coil. In one embodiment, the electronics and coils are implanted separately and connected by an implanted cable. In some embodiments, external controller 404 can be configured to communicate with the TETS receiver 400 and can be worn by the patient, such as on the patient's wrist. In other embodiments, the external controller can be an electronic computing device such as a personal computer, a tablet, smartphone, or laptop computer.

In one embodiment, the receiver unit 400 further includes a communications antenna 406 disposed along an outer periphery, the antenna being configured to send and receive communications data to and from other electronic devices inside and outside of the body. In one embodiment, the receiver unit further includes an internal rechargeable power source. In various embodiments, the receiver unit 400 of the TET system is configured as a single implanted device including the receive coil, antenna, power source, and associated circuitry. The receiver unit is configured so the implantable medical device can be plugged directly into the unit. The single housing configuration makes implantation easier and faster. Additionally, since there are less implants, and consequently less tunneling in the body and percutaneous defect sites, adverse event risks like bleeding and infection are reduced. One of skill will appreciate from the description herein that various internal components of the system can be bundled together or implanted separately. For example, the internal rechargeable power source can be implanted separately from the receiver unit and connected by a power cable. The antenna assembly, power source, and receive coil can all be configured in separate hermetically sealed housings. International Pub. No. WO2007/053881A1, U.S. Pub. No. 2014/0005466, and U.S. Pat. No. 8,562,508, the entire contents of which are incorporated herein for all purposes by reference, disclose several exemplary configurations.

Figure 5:
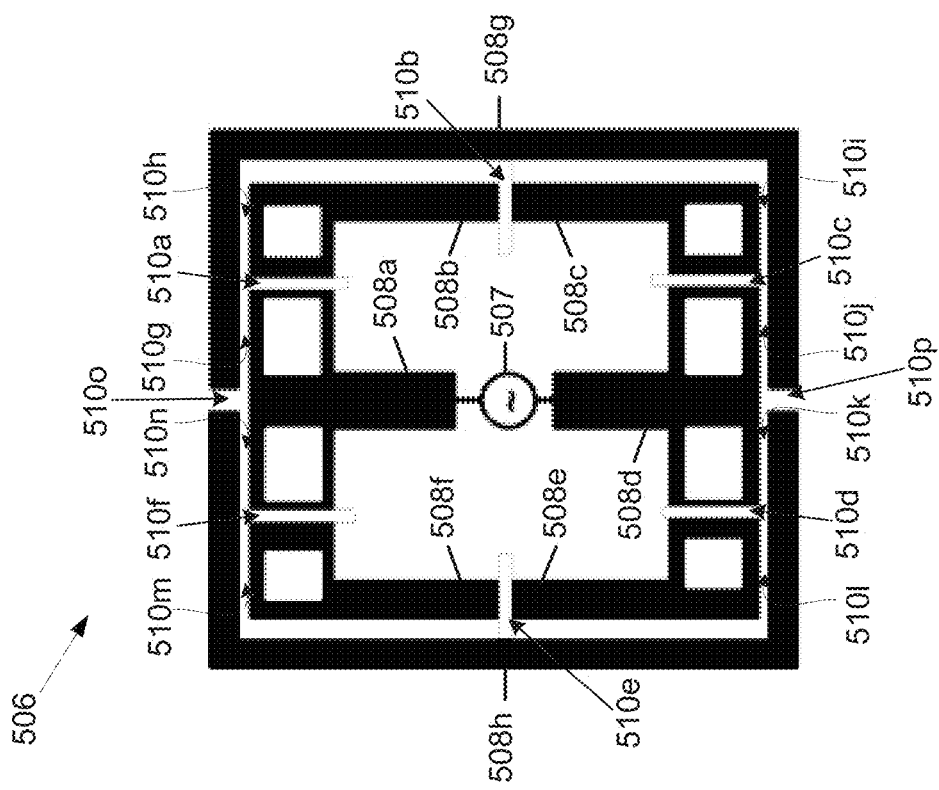
FIG. 5 shows one embodiment of a communications antenna for use with a wireless power transfer system.

FIG. 5 illustrates a top-down view of one embodiment of a communications antenna 506 configured to send and receive communications data from an implanted wireless powered device to external devices. The communications antenna 506 can be disposed on or in the receiver unit illustrated in FIG. 4. The communications antenna 506 can comprise at least one feedline 507 that connects the communications antenna to the radio transmitter and/or receiver, and a plurality of conductive elements 508a-h coupled to the feedline. While conductive elements 508a and 508d are physically connected to the feedline (e.g., with a wire or conductive connection), adjacent conductive elements in the communications antenna are not physically connected, but instead are separated by gaps 510a-p. The gaps can be, for example, air gaps between adjacent conductive elements. More specifically, adjacent conductive elements are not electrically connected to each other, such as with a conductive wire or trace, but instead are separated from each other by the gaps. In the illustrated embodiment, gap 510a separates conductive elements 508a and 508b, gap 510b separates conductive elements 508b and 508c, gap 510c separates conductive elements 508c and 508d, gap 510d separates conductive elements 508d and 508e, gap 510e separates conductive elements 508e and 508f, gap 510f separates conductive elements 508f and 508a. Similarly, gap 510g separates conductive elements 508a and 508g, gap 510h separates conductive elements 508b and 508g, gap 510i separates conductive elements 508c and 508g, gap 510j separates conductive elements 508d and 508g, gap 510k separates conductive elements 508d and 508h, gap 510l separates conductive elements 508e and 508h, gap 510m separates conductive elements 508f and 508h, and gap 510n separates conductive elements 508a and 508h. Finally, gaps 510o and 510p separate conductive elements 508g and 508h on the perimeter of the communications antenna.

As is known in the art, currents can be induced in a loop of conductor or metal when exposed to a magnetic field. Therefore, a looped conductor placed in the TETS field of a magnetically coupled wireless power transfer system can result in potentially large currents being induced in the looped conductor by the TETS field. In this example, an antenna can be saturated by the wireless power transfer. To solve this problem, the communications antennas described herein can include gaps between adjacent conductive elements to minimize low-frequency coupling in the antenna. These antennas can be designed without any closed paths that can be traced to induce currents in the presence of a TETS field. In some embodiments, a wireless power transfer system (such as the system described in FIG. 4) can have a low operating frequency, such as an operating frequency of 250 kHz. By comparison, the communication antenna frequency of the exemplary system is sufficiently higher (e.g., over 100 MHz) such that the TET system does not interfere with the data communication system. Due to the induced power loss in the antenna, especially relative to the loop conductor described above, traditional patch antennas and any antenna with a ground plane would be unsuitable for this application in the presences of a TETS field. The gaps in the communications antenna, therefore, can be configured to prevent induced currents in the antenna during wireless power transfer at this operating frequency. In other words, the exemplary structure includes gaps designed to reduce or minimize low-frequency coupling. The location and spacing of these gaps can be modified and optimized to control the operation and resonant frequencies of the communications antenna relative to the TET system frequency. For example, the width and position of the traces can be changed (e.g. midway through signal flow) to improve performance and coupling at a first frequency range while minimizing coupling at a second frequency range.

In the embodiment of FIG. 5, the conductive elements can comprise a plurality of electrical paths, including an interior trace and an exterior trace. In some embodiments, these electrical paths can be tuned to the same resonant frequencies. In some embodiments, these electrical paths can be tuned to different resonant frequencies. The interior trace can comprise the electrical path from feedline 507 to conductive element 508a, to conductive element 508b, to conductive element 508c, to conductive element 508d, back to feedline 507. The interior trace can also comprise the electrical path from feedline 507 to conductive element 508d, to conductive element 508e, to conductive element 508f, to conductive element 508a, back to feedline 507. Still referring to FIG. 5, the exterior trace can comprise the electrical path from feedline 507 to conductive element 508a, to conductive element 508g along the perimeter of the antenna, to conductive element 508d, back to feedline 507. The exterior trace can also comprise the electrical path from feedline 507 to conductive element 508d, to conductive element 508h along the perimeter of the antenna, to conductive element 508a, back to feedline 507. The choice of interior vs. exterior path, or which path composed of a plurality of conductive elements, depends on the degree to which the path is tuned to resonance at the frequency in question.

As described above, the exemplary communications antenna 506 can comprise two paths, an exterior trace and an interior trace. Each of these paths can be tuned to two different resonant frequencies. If the antenna is driven at the lower of the two resonance frequencies, the RF energy tends to go around the outer path or exterior trace of the antenna. If the antenna is driven at the higher of the two resonance frequencies, the RF energy tends to go around the internal trace of the antenna. When the antenna is driven in the frequencies between two resonance frequencies, the RF energy radiates though both the interior and exterior traces of the antenna. The length of the interior and exterior traces is determined by the wavelength of the radio waves used in the antenna. Since the interior trace can be designed to radiate at a different resonant frequency than the exterior trace, the total length of each trace can be designed based on the needs of the antenna. In some embodiments, both the interior and exterior traces can be configured as quarter-wave antennas, half-wave antennas, 5/8 wave antennas, full-wave antennas, or any other appropriate wavelength. In one specific embodiment, the interior path can comprise a half-wave antenna and the exterior path can comprise a 3/2 wave antenna. In some embodiments, the electrical length of the interior trace can be different than the electrical length of the exterior trace. For example, the interior trace can comprise a half-wave antenna, and the exterior trace can comprise a full-wave antenna, or other appropriate combinations.

As shown in FIG. 5, communications antenna 506 can be mirrored along one or more lines of symmetry. Symmetrical designs tend to create symmetrical radiation patterns. In this embodiment, the top/bottom symmetry is strongly suggested by the symmetry of the feed points 607. In the illustrated embodiment, the top portion of the antenna (conductive elements 508h, 508f, 508a, 508b, and 508g) can mirror the bottom portion of the antenna (conductive elements 508h, 508e, 508d, 508c, and 508g). Similarly, in FIG. 5, the left portion of the antenna (conductive elements 508h, 508f, 508e, 508a, and 508d) can mirror the right portion of the antenna (conductive elements 508g, 508b, 508c, 508d, and 508a).

Figure 6:
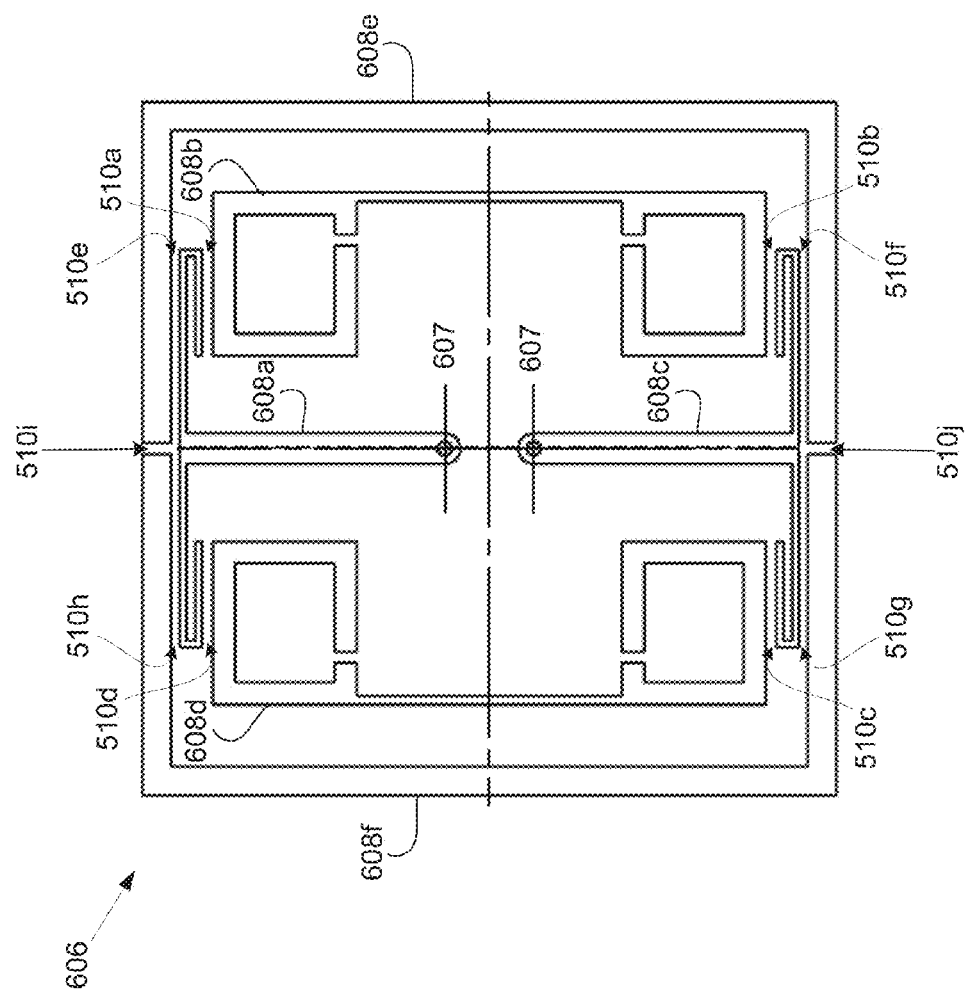
FIG. 6 shows another embodiment of a communications antenna for use with a wireless power transfer system.

FIG. 6 illustrates another embodiment of a communications antenna 606. The antenna 606 is similar to the antenna of FIG. 5, but with a slightly different arrangement of conductive elements. In FIG. 6, antenna 606 includes feedline 607, conductive elements 608a-f, and gaps 510a-j. Similar to the embodiment of FIG. 5, antenna 606 can also include an interior trace and an exterior trace. The electrical path along the interior trace can comprise, for example, a path from the feedline 607 to conductive elements 608a, 608b, 608c, back to feedline 607 (or reversed), or alternatively, a path from the feedline 607 to conductive elements 608c, 608d, 608a, back to feedline 607 (or reversed). Similarly, the electrical path along the exterior trace can comprise, for example, a path from the feedline 607 to conductive elements 608a, 608e, 608c, back to feedline 607 (or reversed), or alternatively, a path from the feedline 607 to conductive elements 608c, 608f, 608a, back to feedline 607 (or reversed). As described above, the interior and exterior traces of the antenna can be tuned to different resonant frequencies. Also shown in FIG. 6, the conductive elements can have a looping design wherein the individual conductive elements are bent or turned so as to arrive at the desired antenna length. It should be noted that even when the conductive elements are bent into a loop-like shape, the loop is not closed and includes a small gap so as to prevent the induction of low-frequency current in the elements. However, high-frequency (antenna frequency) currents must flow or the antenna doesn't radiate.

Figure 7:
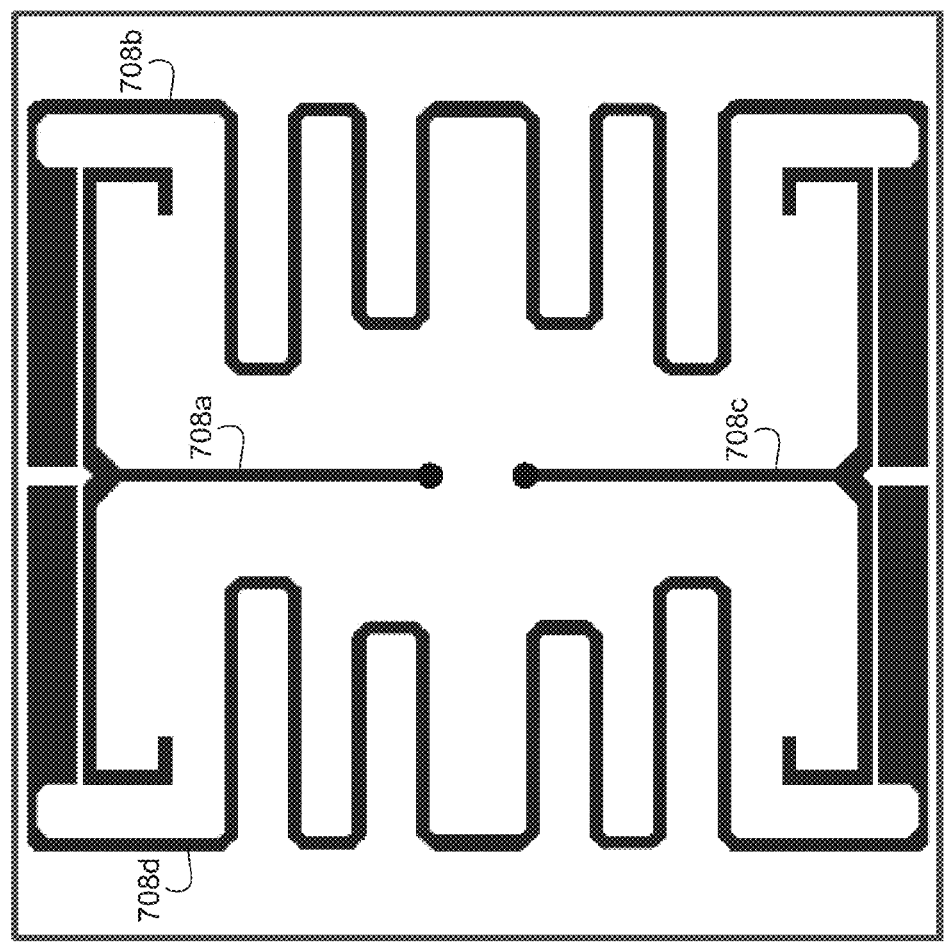
FIG. 7 shows yet another embodiment of a communications antenna for use with a wireless power transfer system.

FIG. 7 illustrates one embodiment in which one or more of the conductive elements 708a-d can include a meander or meandering design, in which the conductive element zigzags in different directions to achieve the desired electrical length.

Figure 8:
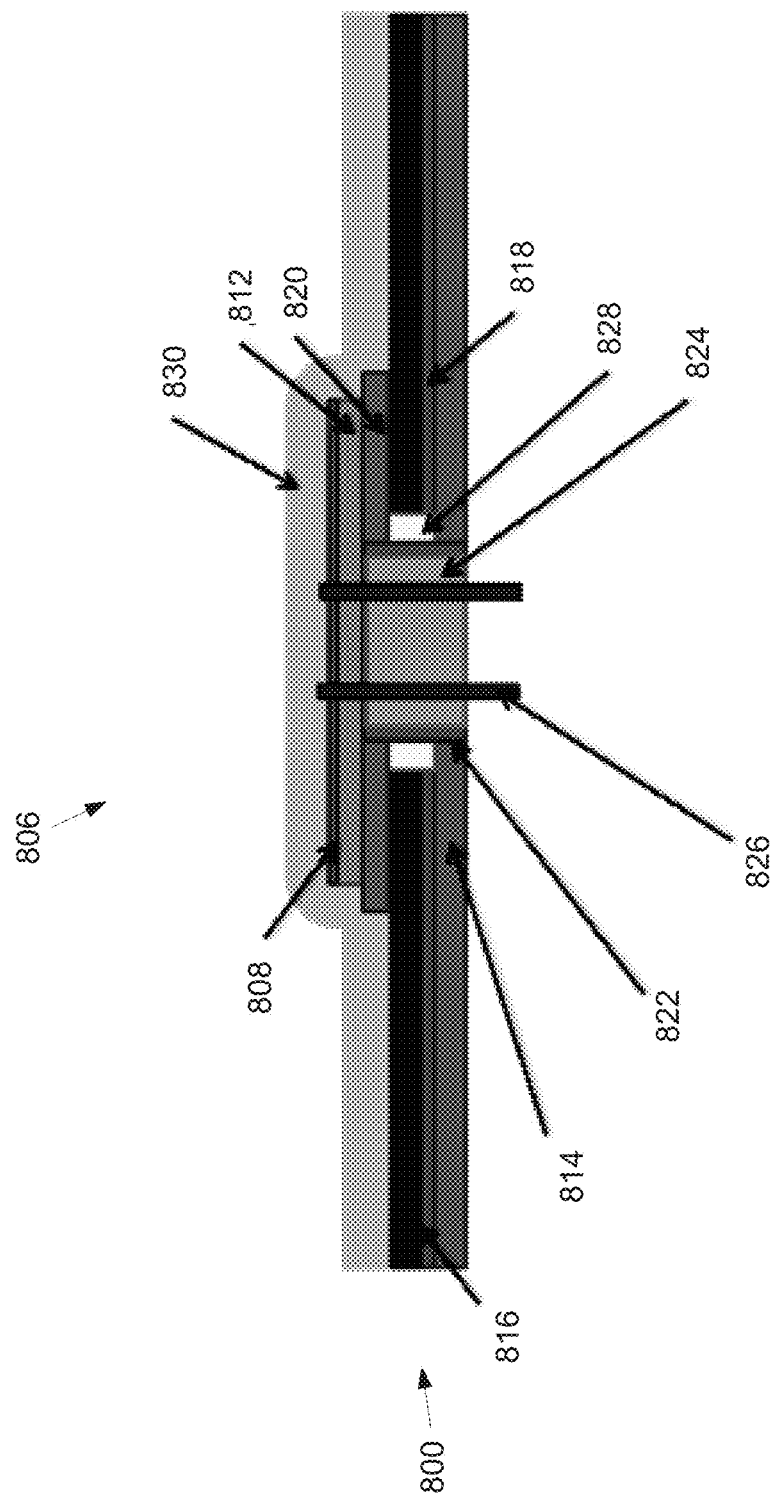
FIG. 8 shows a cross-sectional view of a communications antenna for use with a wireless power transfer system.

FIG. 8 is a cross-sectional view of a communications antenna 806 mounted on a receiver unit 800 (such as the receiver unit of FIG. 4). The antenna 806 can comprise a plurality of conductive elements 808 which make up the resonators of the antenna. The exemplary antenna does not comprise a ground plane. The conductive elements can comprise any conductive material, such as aluminum, copper, silver, gold, or the like. The conductive elements can rest on an antenna body 812. The antenna body can comprise an insulator, such as ceramics, glasses, certain polymers, ceramic powders, glass fibers bonded with polymers, mineral or mineral oxide crystals (sapphire, diamond), or the like. In some embodiments, the antenna body can have a high dielectric constant configured to cause the antenna to appear electrically larger.

In the exemplary embodiment, the receiver unit 800 is a fully integrated antenna. A resonant structure is integrated into the antenna structure without the use of a ground plane. The exemplary receiver unit 800 includes a housing or can 814 comprising a biocompatible material such as titanium. The housing 814 can be hermetically sealed to contain the receiving and power management electronics of the receiver unit. In some embodiments, the housing 814 can be surrounded with a low-frequency ferrite material 816, which can be held in place over the housing 814 with an adhesive layer 818. The low-frequency ferrite material can be configured to prevent the magnetic fields of the wireless power system from exciting circulating currents in the housing. For example, the low-frequency ferrite material can be configured to block or diminish magnetic fields in the operating frequency of the wireless power system (e.g., frequencies in the range of 250 kHz).

A high-frequency ferrite material 820 can be disposed between the antenna body 812 and the low-frequency ferrite material 816. In some embodiments, the low-frequency ferrite material 816 can be extremely lossy at the frequencies used by the communications antenna. The high-frequency ferrite material can serve as a spacer to separate the antenna from the low-frequency ferrite material of the receiver unit, and can also serve to reflect the downward facing energy from the communications antenna back upwards towards the intended communications target. This high-frequency ferrite material can prevent the downward facing energy from being dissipated by the low-frequency ferrite material. In some embodiments, the high-frequency ferrite material can have a low permeability and permittivity. The entire assembly, including the antenna 806 and the receiver unit 800 can be encapsulated with an encapsulation layer 730, which can comprise a plastic, ceramic, or adhesive material.

A feedthrough subassembly comprising a conductive well 822, feedthrough ceramics 824, and feedthrough pins 826, is designed to behave as controlled impedance transmission line between the electronics of the receiver unit and the communications antenna. A clearance layer 828 can be included during manufacturing for mechanical tolerance, and can provide an empty space that is backfilled with an adhesive to ensure that all the components fit together properly.

In FIG. 8, the antenna and housing design can include an inductor configured to shunt any TETS energy picked up by the antenna away from the electronics inside the can. In some embodiments, there may be some finite pickup of the TETS signal by the antenna even with the gaps separating the conductive elements. The inductor value should be as large as possible to shunt away any energy picked up. In some embodiments, the self-resonant frequency of the inductor is 25% higher than the RF frequency of the antenna. In some embodiments, the self-resonant frequency of the inductor is at least 5% higher, at least 10% higher, at least 15% higher, or at least 20% higher than the RF frequency of the antenna. In some embodiments, the self-resonant frequency of the inductor is at least 50% higher than the RF frequency of the antenna. In some embodiments, the self-resonant frequency of the inductor is an order of magnitude higher than the RF frequency of the antenna.

Figure 9:
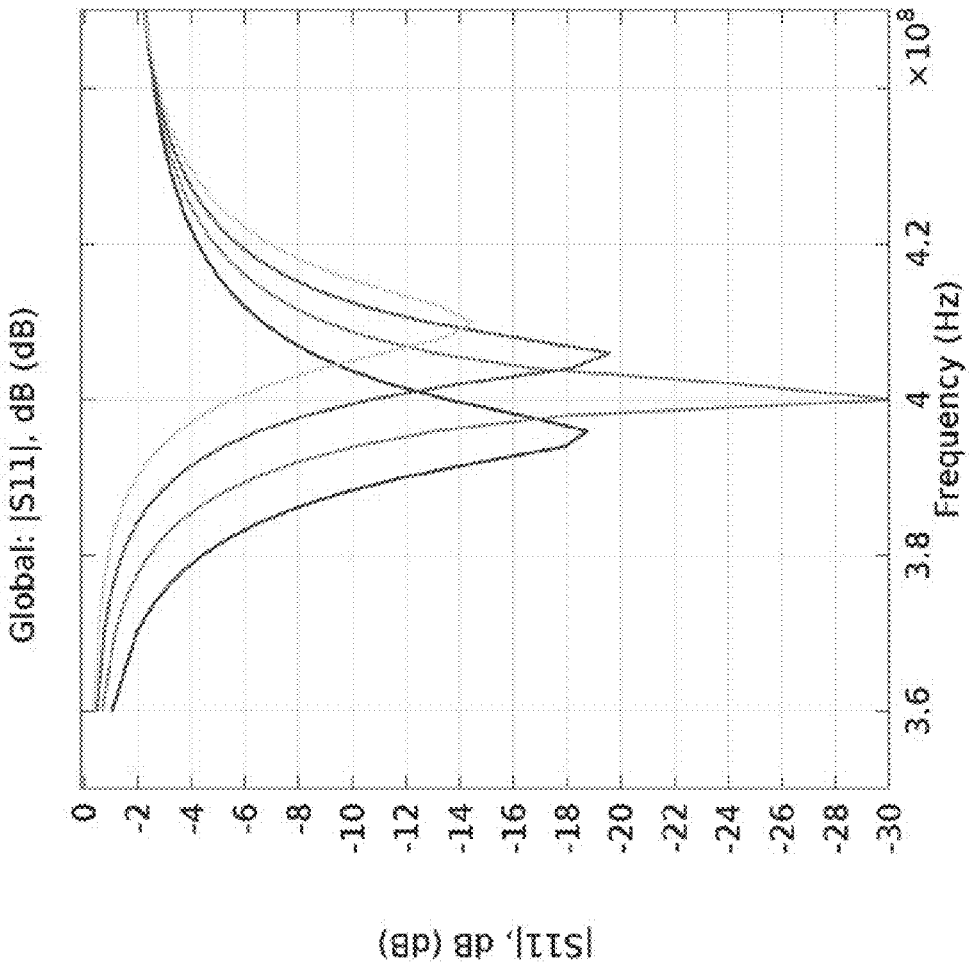
FIG. 9 illustrates antenna match parameterized with increasing gap between conductive elements of a communications antenna.

FIG. 9 illustrates antenna match (return loss) parameterized with increasing gap between the conductive elements of the antenna. The resonance frequency can be adjusted by varying the meander portion of the pattern, but typically multiple parameters should be adjusted in concert to tune performance. In one embodiment, a lower value of return loss is desired in the antenna design.

Figure 10:
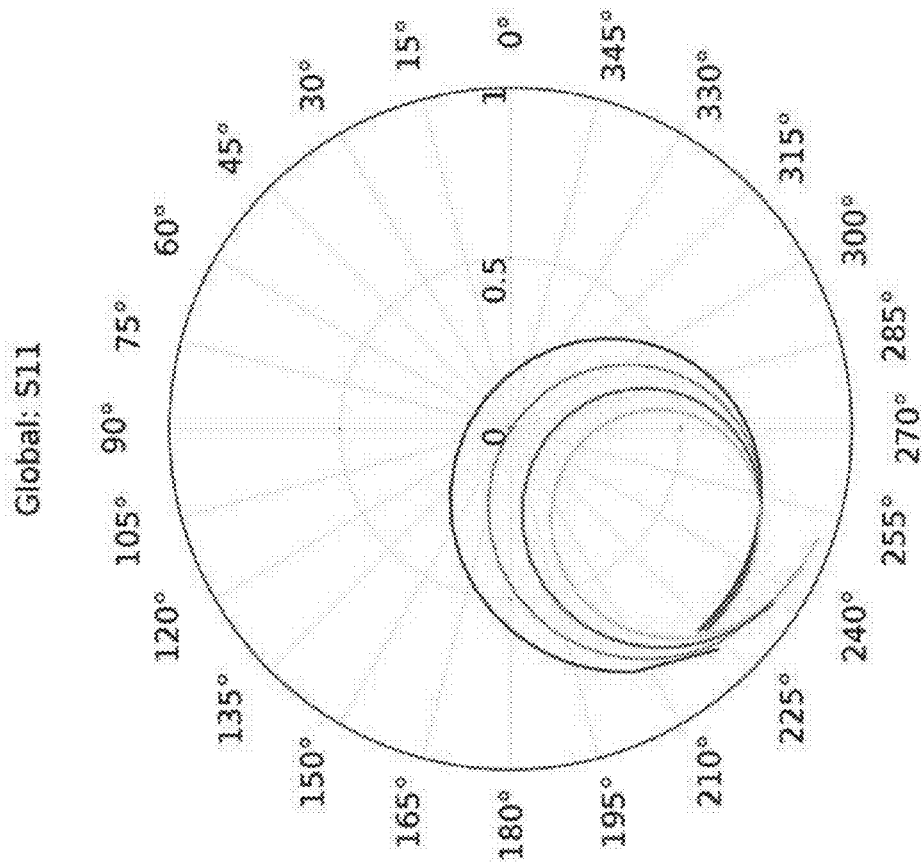
FIG. 10 illustrates antenna match (reflection coefficient) parameterized with increasing gap.

FIG. 10 illustrates antenna match (reflection coefficient) parameterized with increasing gap. A value close to the center (0) is desired in the antenna design. This is the same data as shown in FIG. 9, but plotted as complex reflection.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims. Although described in some respects as a medical system, one will appreciate from the description herein that the principles can apply equally to other types of systems including, but not limited to, consumer electronics, automotive, phones and personal communication devices, gaming devices, and computers and peripherals.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An antenna for use in a wireless power system, comprising:
    a differential transmission line;
    a plurality of conductive elements coupled to the differential transmission line and configured to radiate RF energy to transmit and receive radio information, wherein a first conductive element of the plurality of conductive elements and a second conductive element of the plurality of conductive elements are physically coupled to the differential transmission line, wherein remaining conductive elements of the plurality of conductive elements are not physically coupled to the differential transmission line, wherein a first subset of the plurality of conductive elements defines a first electrical path comprising an interior trace of the antenna, wherein a second subset of the plurality of conductive elements defines a second electrical path comprising an exterior trace of the antenna, wherein the first subset is different from the second subset, and wherein the first and second subsets both include the first conductive element and the second conductive element; and
    a plurality of gaps positioned between adjacent conductive elements, the gaps configured to prevent or reduce induction of current in the plurality of conductive elements when the antenna is exposed to a magnetic field.

2. The antenna of claim 1, wherein the first electrical path is tuned to a first resonant frequency, and the second electrical path is tuned to a second resonant frequency.

3. A wireless receiver for use in a TET system, comprising:
    a hermetically sealed housing;
    receiver electronics contained in the hermetically sealed housing;
    a low-frequency ferrite material surrounding the hermetically sealed housing, the low-frequency ferrite material configured to reduce the amount of magnetic flux that reaches the hermetically sealed housing;
    an antenna body coupled to the low-frequency ferrite material;
    a plurality of conductive elements disposed on the antenna body;
    a differential transmission line electrically connecting the plurality of conductive elements to the receiver electronics and configured to deliver RF energy to the plurality of conductive elements to transmit and receive radio information; and
    a plurality of gaps positioned between adjacent conductive elements, the gaps configured to prevent or reduce induction of current in the plurality of conductive elements when the antenna is exposed to a magnetic field.

4. The wireless receiver of claim 3, wherein the plurality of conductive elements define a first electrical path and a second electrical path.

5. The wireless receiver of claim 4, wherein the first electrical path comprises an interior trace of the antenna, and the second electrical path comprises an exterior trace of the antenna.

6. The wireless receiver of claim 5, wherein the first electrical path is tuned to a first resonant frequency, and the second electrical path is tuned to a second resonant frequency.

7. The wireless receiver of claim 3, further comprising a high-frequency ferrite material positioned between the plurality of conductive elements and the low-frequency ferrite material.

8. A communications antenna, comprising:
    a differential transmission line;
    a plurality of conductive elements coupled to the differential transmission line and configured to radiate RF energy to transmit and receive radio information, wherein a first conductive element of the plurality of conductive elements and a second conductive element of the plurality of conductive elements are physically coupled to the differential transmission line, wherein remaining conductive elements of the plurality of conductive elements are not physically coupled to the differential transmission line, wherein a first subset of the plurality of conductive elements defines a first electrical path comprising an interior trace of the antenna, wherein a second subset of the plurality of conductive elements defines a second electrical path comprising an exterior trace of the antenna, wherein the first subset is different from the second subset, and wherein the first and second subsets both include the first conductive element and the second conductive element; and a plurality of gaps positioned between adjacent conductive elements, the gaps configured to prevent or reduce induction of current in the plurality of conductive elements when the antenna is exposed to a magnetic field.

\* \* \* \* \*

UNITED STATES PATENT AND TRADEMARK OFFICE
CERTIFICATE OF CORRECTION

PATENT NO. : 10,186,760 B2  
APPLICATION NO. : 14/861977  
DATED : January 22, 2019  
INVENTOR(S) : Kevin G. Heppell Page 1 of 1

It is certified that error appears in the above-identified patent and that said Letters Patent is hereby corrected as shown below:

On the Title Page

Item [73], delete "Thoratec Corporation" and insert --TC1 LLC--.

Signed and Sealed this  
Nineteenth Day of February, 2019

Andrei Iancu  
*Director of the United States Patent and Trademark Office*